United States Patent [19]
Villhauer

[11] Patent Number: 6,110,949
[45] Date of Patent: *Aug. 29, 2000

[54] N-(SUBSTITUTED GLYCYL)-4-CYANOTHIAZOLIDINES, PHARMACEUTICAL COMPOSITIONS CONTAINING THEM AND THEIR USE IN INHIBITING DIPEPTIDYL PEPTIDASE-IV

[75] Inventor: Edwin Bernard Villhauer, Morristown, N.J.

[73] Assignee: Novartis AG, Basel, Switzerland

[ * ] Notice: This patent issued on a continued prosecution application filed under 37 CFR 1.53(d), and is subject to the twenty year patent term provisions of 35 U.S.C. 154(a)(2).

[21] Appl. No.: 09/339,503

[22] Filed: Jun. 24, 1999

[51] Int. Cl.$^7$ .................................................. C07D 207/00
[52] U.S. Cl. ........................................... 514/365; 548/200
[58] Field of Search ............................... 548/200; 514/365

[56] References Cited

U.S. PATENT DOCUMENTS 5,939,560  8/1999  Jenkins ..................................... 548/535

FOREIGN PATENT DOCUMENTS

| | | |
|---|---|---|
| 555 824 | 8/1993 | European Pat. Off. . |
| 1581 09 | 12/1982 | Germany . |
| 296 075 | 11/1991 | Germany . |
| 90/12005 | 10/1990 | WIPO . |
| 91/16339 | 10/1991 | WIPO . |
| 93/08259 | 4/1993 | WIPO . |
| 95/11689 | 5/1995 | WIPO . |
| 95/13069 | 5/1995 | WIPO . |
| 95/15309 | 6/1995 | WIPO . |
| 95/29190 | 11/1995 | WIPO . |
| 95/29691 | 11/1995 | WIPO . |
| 95/34538 | 12/1995 | WIPO . |
| 98/19998 | 5/1998 | WIPO . |
| 99/38501 | 8/1999 | WIPO . |

OTHER PUBLICATIONS

Archives of Biochemistry and Biophysics, vol. 323, No. 1, pp. 148–154 (1995).
Journal of Neurochemistry, vol. 66, pp. 2105–2112 (1996).
Bulletin of the Chemical Society of Japan, vol. 50, No. 7, pp. 1827–1830 (1977).
Bulletin of the Chemical Society of Japan, vol. 51, No. 3, pp. 878–883 (1978).
Derwent Abstract 95: 302548.
Derwent Abstract 84: 177689.
Derwent Abstract 96: 116353.
Biochimica et Biophysica, vol. 1293, pp. 147–153.
Bioorganic and Medicinal Chemistry Letters, vol. 6, No. 10, pp. 1163–1166 (1996).
J.Med.Chem., vol. 39, pp. 2087–2094 (1996).
Diabetes, vol. 44, pp. 1126–1131 (Sep.'96).
Bioorganic and Medicinal Chemistry Letters. vol. 6, No. 22, pp. 2745–2748 (1996).
Eur. J. Med. Chem., vol. 32, pp. 301–309 (1997).
Biochemistry, vol. 38, pp. 11597–11603 (1999).

*Primary Examiner*—Robert Gerstl
*Attorney, Agent, or Firm*—Joseph J. Borovian

[57] ABSTRACT

The invention discloses certain N-(substituted glycyl)-4-cyanothiazolidines, pharmaceutical compositions containing said compounds as an active ingredient thereof, and the use of said compounds in inhibiting dipeptidyl peptidase-IV.

38 Claims, No Drawings

N-(SUBSTITUTED GLYCYL)-4-CYANOTHIAZOLIDINES, PHARMACEUTICAL COMPOSITIONS CONTAINING THEM AND THEIR USE IN INHIBITING DIPEPTIDYL PEPTIDASE-IV

FIELD OF THE INVENTION

The present invention relates to the area of dipeptidyl peptidase-IV inhibition and, more particularly, relates to certain N-(substituted glycyl)-4-cyanothiazolidines, pharmaceutical compositions containing said compounds, and the use of said compounds in inhibiting dipeptidyl peptidase-IV.

BACKGROUND OF THE INVENTION

Dipeptidyl peptidase-IV (DPP-IV) is a serine protease which cleaves N-terminal dipeptides from a peptide chain containing, preferably, a proline residue in the penultimate position. Although the biological role of DPP-IV in mammalian systems has not been completely established, it is believed to play an important role in neuropeptide metabolism, T-cell activation, attachment of cancer cells to the endothelium and the entry of HIV into lymphoid cells.

More recently, it was discovered that DPP-IV is responsible for inactivating glucagon-like peptide-1 (GLP-1). More particularly, DPP-IV cleaves the amino-terminal His-Ala dipeptide of GLP-1, generating a GLP-1 receptor antagonist, and thereby shortens the physiological response to GLP-1. Since the half-life for DPP-IV cleavage is much shorter than the half-life for removal of GLP-1 from circulation, a significant increase in GLP-1 bioactivity (5- to 10-fold) is anticipated from DPP-IV inhibition. Since GLP-1 is a major stimulator of pancreatic insulin secretion and has direct beneficial effects on glucose disposal, DPP-IV inhibition appears to represent an attractive approach for treating non-insulin-dependent diabetes mellitus (NIDDM).

Although a number of DPP-IV inhibitors have been described in the literature, all have limitations relating to potency, stability or toxicity. Accordingly, it is clear that a great need exists for novel DPP-IV inhibitors which are useful in treating conditions mediated by DPP-IV inhibition and which do not suffer from the above-mentioned limitations of known DPP-IV inhibitors.

DESCRIPTION OF THE PRIOR ART

WO 95/15309 discloses certain peptide derivatives which are inhibitors of DPP-IV and, therefore, are useful in treating a number of DPP-IV mediated processes.

WO 95/13069 discloses certain cyclic amine compounds which are useful in stimulating the release of natural or endogenous growth hormone.

European Patent 555,824 discloses certain benzimidazolyl compounds which prolong thrombin time and inhibit thrombin and serine-related proteases.

Archives of Biochemistry and Biophysics, Vol. 323, No. 1, pgs. 148–154 (1995) discloses certain aminoacylpyrrolidine-2-nitriles which are useful as DPP-IV inhibitors.

Journal of Neurochemistry, Vol. 66, pgs. 2105–2112 (1996) discloses certain Fmoc-aminoacylpyrrolidine-2-nitriles which are useful in inhibiting prolyl oligopeptidase.

Bulletin of the Chemical Society of Japan, Vol. 50, No. 7, pgs. 1827–1830 (1977) discloses the synthesis of an aminohexapeptide, viz., Z-Val-Val-lmPro-Gly-Phe-Phe-OMe, and its related aminopeptides. In addition, the antimicrobial properties of said compounds were examined.

Bulletin of the Chemical Society of Japan, Vol. 51, No. 3, pgs. 878–883 (1978) discloses the synthesis of two known peptide antibiotics, viz., Bottromycins $B_1$ and $B_2$ according to the structures proposed by Nakamura, et al. However, since the resultant compounds were devoid of antimicrobial properties, it was concluded that the structures proposed by Nakamura, et al. were erroneous.

WO 90/12005 discloses certain amino acid compounds which inhibit prolylendopeptidase activity and, therefore, are useful in treating dementia or amnesia.

Derivent Abstract 95: 302548 discloses certain N-(aryl (alkyl)carbonyl) substituted heterocyclic compounds which are cholinesterase activators with enhanced peripheral selectivity useful in treating conditions due to the lowering of cholinesterase activity.

Derivent Abstract 84: 177689 discloses certain 1-acyl-pyrrolidine-2-carbonitrile compounds which are useful as intermediates for proline compounds exhibiting angiotensin converting enzyme (ACE) inhibiting activity.

Derivent Abstract 96: 116353 discloses certain 3-amino-2-mercapto-propyl-proline compounds which are Ras farnesyl-transferase inhibitors useful in treating various carcinomas or myeloid leukemias.

WO 95/34538 discloses certain pyrrolidides, phosphonates, azetidines, peptides and azaprolines which inhibit DPP-IV and, therefore, are useful in treating conditions mediated by DPP-IV inhibition.

WO 95/29190 discloses certain compounds characterized by a plurality of KPR-type repeat patterns carried by a peptide matrix enabling their multiple presentation to, and having an affinity for, the enzyme DPP-IV, which compounds exhibit the ability to inhibit the entry of HIV into cells.

WO 91/16339 discloses certain tetrapeptide boronic acids which are DPP-IV inhibitors useful in treating autoimmune diseases and conditions mediated by IL-2 suppression.

WO 93/08259 discloses certain polypeptide boronic acids which are DPP-IV inhibitors useful in treating autoimmune diseases and conditions mediated by IL-2 suppression.

WO 95/11689 discloses certain tetrapeptide boronic acids which are DPP-IV inhibitors useful in blocking the entry of HIV into cells.

East German Patent 158109 discloses certain N-protected peptidyl-hydroxamic acids and nitrobenzoyloxamides which are useful as, inter alia, DPP-IV inhibitors.

WO 95/29691 discloses, inter alia, certain dipeptide proline phosphonates which are DPP-IV inhibitors useful in the treatment of immune system disorders.

East German Patent 296075 discloses certain amino acid amides which inhibit DPP-IV.

Biochimica et Biophysica Acta, Vol. 1293, pgs. 147–153 discloses the preparation of certain di- and tri-peptide p-nitroanilides to study the influence of side chain modifications on their DPP-IV and PEP-catalyzed hydrolysis.

Bioorganic and Medicinal Chemistry Letters, Vol. 6, No. 10, pgs. 1163–1166 (1996) discloses certain 2-cyanopyrrolidines which are inhibitors of DPP-IV.

J. Med. Chem., Vol. 39, pgs. 2087–2094 (1996) discloses certain prolineboronic acid-containing dipeptides which are inhibitors of DPP-IV.

Diabetes, Vol. 44, pgs. 1126–1131 (September 1996) is directed to a study which demonstrates that GLP-I amide is rapidly degraded when administered by subcutaneous or intravenous routes to diabetic and non-diabetic subjects.

Bioorganic and Medicinal Chemistry Letters, Vol. 6, No. 22, pgs. 2745–2748 (1996) discloses certain 4-cyanothiazolidides which are inhibitors of DPP-IV.

Eur J. Med. Chem., Vol. 32, pgs. 301–309 (1997) discloses certain homologues and 3-substituted analogues of pyrrolidides and thiazolidides which inhibit DPP-IV.

SUMMARY OF THE INVENTION

The present invention provides new DPP-IV inhibitors which are effective in treating conditions mediated by DPP-IV inhibition. More particularly, the present invention relates to certain N-(substituted glycyl)-4-cyanothiazolidines which inhibit DPP-IV. In addition, the present invention provides pharmaceutical compositions useful in inhibiting DPP-IV comprising a therapeutically effective amount of a certain N-(substituted glycyl)-4-cyano-thiazolidine. Moreover, the present invention provides a method of inhibiting DPP-IV comprising administering to a mammal in need of such treatment a therapeutically effective amount of a certain N-(substituted glycyl)-4-cyanothiazolidine.

DETAILED DESCRIPTION OF THE INVENTION

The essence of the instant invention is the discovery that certain N-(substituted glycyl)-4-cyanothiazolidines are useful in inhibiting DPP-IV. In one embodiment, the present invention provides compounds of formula I:

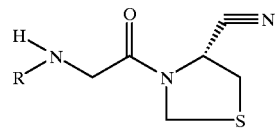

I wherein

R is $C_{1-12}$alkyl; a group

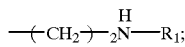

an unsubstituted $(C_{3-7})$cycloalkyl ring; a group —(—CH$_2$—)—$_2$R$_2$; a group

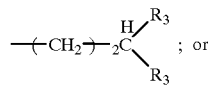

a group —(—CH$_2$—)—$_3$R$_4$;

R$_1$ is an unsubstituted pyridine ring; a pyridine ring mono- or di-substituted by halo, trifluoromethyl, cyano or nitro; an unsubstituted pyrimidine ring; or a pyrimidine ring monosubstituted by halo, trifluoromethyl, cyano or nitro;

R$_2$ is an unsubstituted phenyl ring; or a phenyl ring mono-, di- or tri-substituted by halo or $(C_{1-3})$alkoxy;

each R$_3$, independently, is an unsubstituted phenyl ring; or a phenyl ring monosubstituted by halo or $(C_{1-3})$alkoxy; and R$_4$ is a 2-oxopyrrolidine group or a $(C_{2-4})$alkoxy group;

or a pharmaceutically acceptable acid addition salt thereof.

Preferred compounds are those of formula Ia:

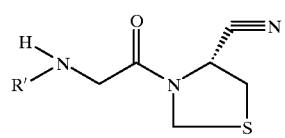

Ia where

R' is $C_{1-10}$alkyl; a group

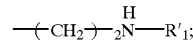

an unsubstituted $(C_{3-7})$cycloalkyl ring; or a group —(—CH$_2$—)—$_3$R$_4$';

R$_1$' is an unsubstituted pyridine ring; or a pyridine ring mono- or di- substituted by halo, trifluoromethyl, cyano or nitro; and R$_4$' is a $(C_{2-4})$alkoxy group;

or a pharmaceutically acceptable acid addition salt thereof.

More preferred compounds are those of formula Ib:

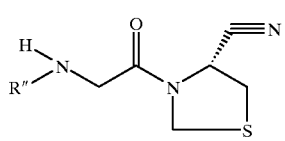

Ib where

R" is $C_{1-8}$alkyl; a group

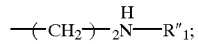

an unsubstituted $(C_{4-6})$—cycloalkyl ring; or a group —(—CH$_2$—)—$_3$R$_4$';

R$_1$" is a pyridine ring mono- or di-substituted by halo, trifluoromethyl, cyano or nitro; and R$_4$' is as defined above;

or a pharmaceutically acceptable acid addition salt thereof.

Even more preferred compounds are those of formula Ic:

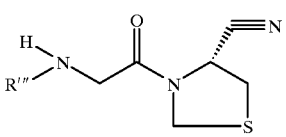

Ic where

R'" is $C_{1-6}$alkyl; a group

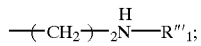

an unsubstituted $(C_{4-6})$—cycloalkyl ring; or a group —(—CH$_2$—)—$_3$R$_4$';

R'" is a pyridine ring monosubstitued by halo, trifluoromethyl, cyano or nitro; and $R_4'$ is as defined above;
or a pharmaceutically acceptable acid addition salt thereof.

In another embodiment, the instant invention provides pharmaceutical compositions useful in inhibiting DPP-IV comprising a pharmaceutically acceptable carrier or diluent and a therapeutically effective amount of a compound of formula I above, or a pharmaceutically acceptable acid addition salt thereof, preferably a compound of formula Ia above, or a pharmaceutically acceptable acid addition salt thereof, more preferably a compound of formula Ib above, or a pharmaceutically acceptable acid addition salt thereof, and even more preferably a compound of formula Ic above, or a pharmaceutically acceptable acid addition salt thereof.

In still another embodiment, the instant invention provides a method of inhibiting DPP-IV comprising administering to a mammal in need of such treatment a therapeutically effective amount of a compound of formula I above, or a pharmaceutically acceptable acid addition salt thereof, preferably a compound of formula Ia above, or a pharmaceutically acceptable acid addition salt thereof, more preferably a compound of formula Ib above, or a pharmaceutically acceptable acid addition salt thereof, and even more preferably a compound of formula Ic above, or a pharmaceutically acceptable acid addition salt thereof.

In a further embodiment, the instant invention provides a method of treating conditions mediated by DPP-IV inhibition comprising administering to a mammal in need of such treatment a therapeutically effective amount of a compound of formula I above, or a pharmaceutically acceptable acid addition salt thereof, preferably a compound of formula Ia above, or a pharmaceutically acceptable acid addition salt thereof, more preferably a compound of formula Ib above, or a pharmaceutically acceptable acid addition salt thereof, and even more preferably a compound of formula Ic above, or a pharmaceutically acceptable acid addition salt thereof.

In the above definitions, it should be noted that the "alkyl" and "alkoxy" significances are either straight or branched chain, of which examples of the latter are isopropyl and t-butyl.

The acid addition salts of the compounds of formula I may be those of pharmaceutically acceptable organic or inorganic acids. Although the preferred acid addition salts are the hydrochlorides, salts of methanesulfonic, sulfuric, phosphoric, citric, lactic and acetic acid may also be utilized.

The compounds of formula I may be prepared by the following three-step reaction:

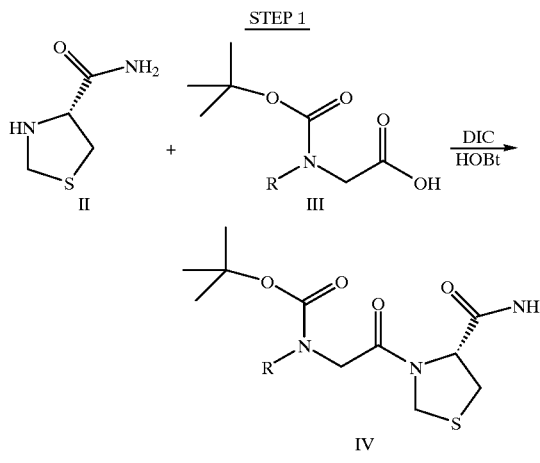

where R is as defined above.

As to the individual steps, Step 1 involves the coupling of an N-t-boc protected N-substituted glycine compound of formula III with a slight molar excess of the amide compound of formula II employing 1,3-diisopropylcarbodiimide as the coupling agent and 1-hydrobenzotriazole hydrate as the activator therefor to obtain a t-boc protected amide compound of formula IV. The coupling reaction is conducted in the presence of an inert, organic solvent, preferably a cyclic ether such as tetrahydrofuran, at a temperature of from 10° to 35° C. for a period of between 8 and 36 hours.

The second step concerns the dehydration of the compound prepared in Step 1, i.e., a t-boc protected amide of formula IV, with between 2.5 and 3 equivalents of phosphoryl chloride to obtain a t-boc protected nitrile compound of formula V. The dehydration is conducted in the presence of a mixture of pyridine and imidazole, at a temperature of from −20° to −45° C. for a period of between 30 minutes and 2.5 hours.

The third step involves the deprotection of the compound prepared in the second step, i.e., a t-boc protected nitrile compound of formula V, employing trifluoroacetic acid as the deprotecting agent to obtain an N-substituted glycyl-4-cyanothiazolidine compound of formula I. The deprotection is carried out in the presence of an inert, organic solvent, preferably a cyclic ether such as tetrahydrofuran, at a temperature of from 10° to 35° C. for a period of between 2 and 6 hours.

The amide compound of formula II may be prepared in accordance with the following four-step reaction scheme:

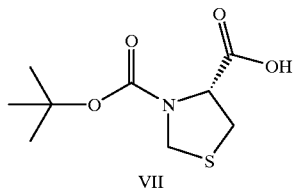

VII

STEP B

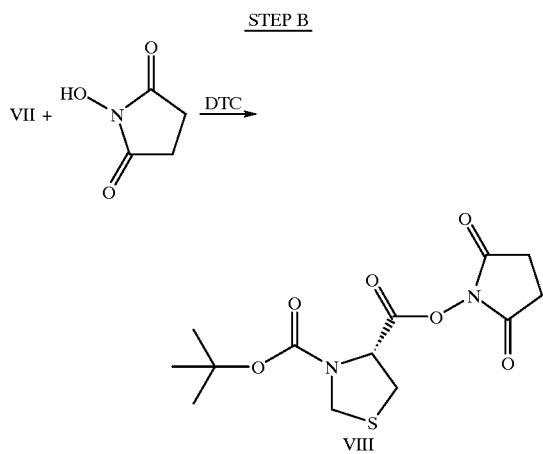

VIII

STEP C

VIII $\xrightarrow{\text{ammonia}}$

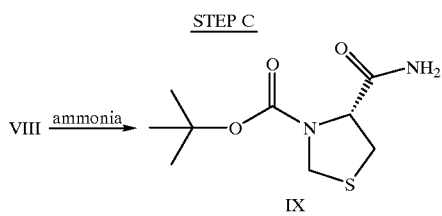

IX

STEP D

IX $\xrightarrow[\text{2) ion-exchange resin}]{\text{1) TFA}}$

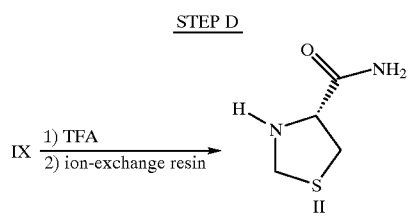

II

With regard to the individual steps, Step A involves the amino protection of the carboxylic acid compound of formula VI employing di-t-butyl dicarbonate as the activating agent to obtain the t-boc protected carboxylic acid compound of formula VII. The reaction is conducted in the presence of an alkali metal base, preferably an alkali metal hydroxide such as sodium hydroxide, and an aqueous mixture comprising a cyclic either, e.g., a mixture of water and dioxane. The reaction is conducted at a temperature of from 10° to 35° C. for a period of between 1 and 4 hours.

Step B concerns the coupling of the compound prepared in Step A, i.e., the t-boc protected carboxylic acid of formula VII, with a slight molar excess of N-hydroxysuccinimide employing 1,3-diisopropylcarbodiimide as the coupling agent to obtain a mixture of the t-boc protected anhydride compound of formula VIII and 1,3-diisopropylurea. The coupling reaction is conducted in the presence of an inert, organic solvent, preferably a cyclic ether such as tetrahydrofuran, at a temperature of from 10° to 35° C. for a period of between 1 and 4 hours.

Step C relates to the amidation of the compound prepared in Step B, i.e., the t-boc protected anhydride of formula VIII, employing ammonia to obtain a mixture of the t-boc protected amide compound of formula IX and 1,3-diisopropylurea. The amidation is conducted in the presence of an inert, organic solvent, preferably an aliphatic halogenated hydrocarbon such as methylene chloride, at a temperature of from 10° to 35° C. for a period of between 2 and 6 hours.

The first part of Step D involves the acidic decarboxylation of the compound prepared in Step C, i.e., the t-boc protected amide compound of formula IX, employing trifluoroacetic acid to obtain a mixture of the trifluoroacetic acid salt of the desired amide compound of formula II and 1,3-diisopropylurea. The acidic decarboxylation is conducted at a temperature of from 10° to 35° C. for a period of between 1 and 4 hours.

The second part of Step D involves subjecting the mixture obtained in the first part to an ion-exchange resin, preferably Amberlite IRA 400(OH), to obtain the amide compound of formula II. The ion-exchange is conducted in the presence of an inert, organic solvent, preferably a cyclic ether such as tetrahydrofuran, at a temperature of from 10° to 35° C. for a period of between 15 and 45 minutes.

The N-t-boc protected N-substituted glycine compounds of formula III may be prepared by the following three-step reaction:

STEP 1A

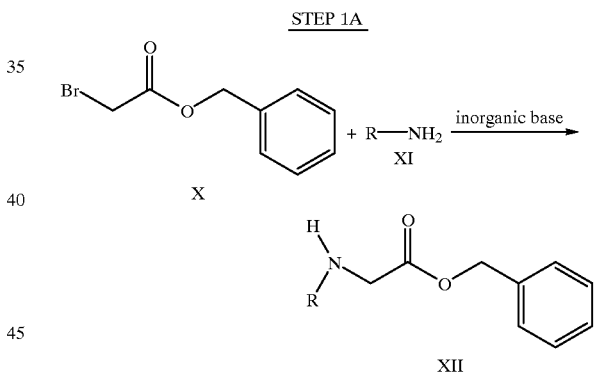

STEP 2A

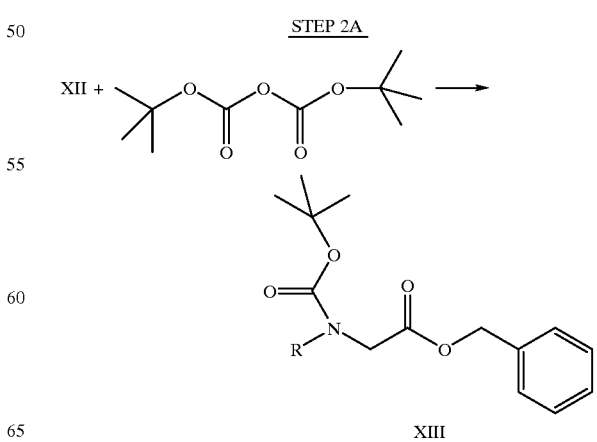

STEP 3A

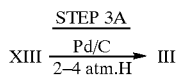

where R is as defined above

As regards to the individual steps, Step 1A involves the coupling of the compound of formula X, viz., benzyl 2-bromoacetate, with at least 3 equivalents of a primary amine compound of formula XI in the presence of an inorganic base, preferably an alkali metal carbonate such as potassium carbonate, to obtain an amine compound of formula XII. The coupling is conducted in the presence of an inert, organic solvent, preferably an aliphatic halogenated hydrocarbon such as methylene chloride, initially at ice-water temperature for a period of between 30 minutes and 5 hours, and then at a temperature of from 10° to 35° C. for a period of between 5 and 60 hours.

Step 2A concerns the amino protection of the compound prepared in Step 1A, i.e., an amine compound of formula XII, employing di-t-butyl dicarbonate as the activating agent to obtain a t-boc protected amine compound of formula XIII. The reaction is conducted in the presence of an inert, organic solvent, preferably an aliphatic halogenated hydrocarbon such as methylene chloride, initially at ice-water temperature for a period of between 30 minutes and 4 hours, and then at a temperature of from 10° to 35° C. for a period of between 6 and 24 hours.

Step 3A involves the deesterification via hydrogenation of the compound prepared in Step 2a, i.e., a t-boc protected amine compound of formula XII, employing a hydrogenation catalyst such as 10% palladium on carbon in the presence of between 2 and 4 atmospheres of hydrogen to obtain an N-t-boc protected N-substituted glycine compound of formula III. The hydrogenation is typically carried out in the presence of an inert, organic solvent typically utilized for this purpose, e.g., ethyl acetate, at a temperature of between 20° and 30° C. for a period of between 12 and 24 hours.

The primary amine compounds of formula XI are known and may be prepared by procedures well documented in the literature. For example: a) 2-[(5-chloropyridin-2-yl)amino]ethylamine can be prepared by refluxing a mixture of 2,5-dichloropyridine with ethylenediamine in an oil bath for a period of between 6 and 12 hours. (b) Similarly, 2-[(5-trifluoromethylpyridin-2-yl)amino]ethylamine can be prepared by refluxing a mixture of 2-chloro-5-trifluoromethyl pyridine with ethylenediamine in an oil bath for a period of between 6 and 12 hours. (c) 2-[(5-cyanopyridin-2-yl)amino]-ethylamine can be prepared by stirring a mixture of 2-chloropyridine-5-carbonitrile and ethylenediamine at a temperature between 20° and 30° C., for a period of between 4 and 6 hours. (d) 2-[(pyrimidin-2-yl)amino]ethylamine can be prepared by adding ethylenediamine to ice-bath cooled 2-chloropyrimidine and allowing the mixture to react at a temperature between 20° and 30° C., for a period of between 12 and 20 hours.

As indicated above, the compounds of formula I form pharmaceutically acceptable acid addition salts. For example, the free base of a compound of formula I can be reacted with hydrochloric acid in gaseous form to form the corresponding mono- and di-hydrochloride salt forms, whereas reacting the free base with methanesulfonic acid forms the corresponding mesylate salt form. All pharmaceutically acceptable acid addition salt forms of the compounds of formula I are intended to be embraced by the scope of this invention.

As indicated above, all of the compounds of formula I, and their corresponding pharmaceutically acceptable acid addition salts, are useful in inhibiting DPP-IV. The ability of the compounds of formula I, and their corresponding pharmaceutically acceptable acid addition salts, to inhibit DPP-IV may be demonstrated employing the Caco-2 DPP-IV Assay which measures the ability of test compounds to inhibit DPP-IV activity from human colonic carcinoma cell extracts. The human colonic carcinoma cell line Caco-2 was obtained from the American Type Culture Collection (ATCC HTB 37). Differentiation of the cells to induce DPP-IV expression was accomplished as described by Reisher, et al. in an article entitled "Increased expression of . . . intestinal cell line Caco-2" in Proc. Natl. Acad. Sci., Vol. 90, pgs. 5757–5761 (1993). Cell extract is prepared from cells solubilized in 10 mM Tris-HCl, 0.15 M NaCl, 0.04 t.i.u. aprotinin, 0.5% nonidet-P40, pH 8.0, which is centrifuged at 35,000 g for 30 min. at 4° C. to remove cell debris. The assay is conducted by adding 20 μg solubilized Caco-2 protein, diluted to a final volume of 125 μl in assay buffer (25 mM Tris-HCl pH 7.4, 140 mM NaCl, 10 mM KCl, 1% bovine serum albumin) to microtiter plate wells. The reaction is initiated by adding 25 μl of 1 mM substrate (H-Alanine-Proline-pNA; pNA is p-nitroaniline). The reaction is run at room temperature for 10 minutes after which time a 19 μl volume of 25% glacial acetic acid is added to stop the reaction. Test compounds are typically added as 30 μl additions and the assay buffer volume is reduced to 95 μl. A standard curve of free p-nitroaniline is generated using 0–500 μM solutions of free pNA in assay buffer. The curve generated is linear and is used for interpolation of substrate consumption (catalytic activity in nmoles substrate cleaved /min). The endpoint is determined by measuring absorbance at 405 nm in a Molecular Devices UV Max microtiter plate reader. The potency of the test compounds as DPP-IV inhibitors, expressed as $IC_{50}$, is calculated from 8-point, dose-response curves using a 4-parameter logistic function.

The following $IC_{50}$s were obtained:

| Compound | Caco-2 DPP-IV (μM) |
|---|---|
| Ex. 1 | 0.007 |
| Ex. 2 | 0.007 |
| Ex. 3 | 0.006 |

The ability of the compounds of formula I, and their corresponding pharmaceutically acceptable acid addition salts, to inhibit DPP-IV may also be demonstrated by measuring the effects of test compounds on DPP-IV activity in human and rat plasma employing a modified version of the assay described by Kubota, et al. in an article entitled "Involvement of dipeptidylpeptidase IV in an in vivo immune response" in Clin. Exp. Immunol., Vol. 89, pgs. 192–197 (1992). Briefly, five μl of plasma are added to 96-well flat-bottom mictotiter plates (Falcon), followed by the addition of 5 μl of 80 mM $MgCl_2$ in incubation buffer (25 mM HEPES, 140 mM NaCl, 1% RIA-grade BSA, pH 7.8). After a 5 min. incubation at room temperature, the reaction is initiated by the addition of 10 μl of incubation buffer containing 0.1 mM substrate (H-Glycine-Proline-AMC; AMC is 7-amino-4-methylcoumarin). The plates are covered with aluminum foil (or kept in the dark) and incubated at room temperature for 20 min. After the 20 min. reaction, fluorescence is measured using a CytoFluor 2350 fluorimeter (Excitation 380 nm Emission 460 nm; sensitivity setting 4). Test compounds are typically added as 2 μl additions and the assay buffer volume is reduced to 13 μl. A fluorescence-concentration curve of free AMC is generated using 0–50 μM solutions of AMC in assay buffer. The curve generated is linear and is used for interpolation of substrate consumption (catalytic activity in nmoles substrate cleaved/min). As with the previous assay, the potency of the test compounds as DPP-IV inhibitors, expressed as $IC_{50}$, is calculated from 8-point, dose-response curves using a 4 parameter logistic function.

The following $IC_{50}$s were obtained:

| Compound | human plasma DPP-IV (μM) | rat plasma DPP-IV (μM) |
|---|---|---|
| Ex. 1 | 0.01 | 0.01 |
| Ex. 2 | 0.005 | 0.001 |
| Ex. 3 | 0.003 | 0.003 |

In view of their ability to inhibit DPP-IV, the compounds of formula I, and their corresponding pharmaceutically acceptable acid addition salts, are useful in treating conditions mediated by DPP-IV inhibition. Based on the above and findings in the literature, it is expected that the compounds disclosed herein are useful in the treatment of non-insulin-dependent diabetes mellitus, arthritis, obesity, allograft rejection in transplantation and calcitonin-osteoporosis. More specifically, for example, the compounds of formula I, and their corresponding pharmaceutically acceptable acid addition salts, improve early insulin response to an oral glucose challenge and, therefore, are useful in treating non-insulin-dependent diabetes mellitus. The ability of the compounds of formula I, and their corresponding pharmaceutically acceptable acid addition salts, to improve early insulin response to an oral glucose challenge may be measured in insulin resistant rats according to the following method:

Male Sprague-Dawley rats that had been fed a high fat diet (saturated fat=57% calories) for 2–3 weeks were fasted for approximately 2 hours on the day of testing, divided into groups of 8–10, and dosed orally with 10 μmol/kg of the test compounds in CMC. An oral glucose bolus of 1 g/kg was administered 30 minutes after the test compound directly into the stomach of the test animals. Blood samples, obtained at various timepoints from chronic jugular vein catheters were analyzed for plasma glucose and immunoreactive insulin (IRI) concentrations, and plasma DPP-IV activity. Plasma insulin levels were assayed by a double antibody radioimmunoassay (RIA) method using a specific anti-rat insulin antibody from Linco Research (St. Louis, Mo.). The RIA has a lower limit of detection of 0.5 μU/ml with intra- and inter-assay variations of less than 5%. Data are expressed as % increase of the mean of the control animals. Upon oral administration, each of the compounds tested amplified the early insulin response which led to an improvement in glucose tolerance in the insulin resistant test animals.

The precise dosage of the compounds of formula I, and their corresponding pharmaceutically acceptable acid addition salts, to be employed for treating conditions mediated by DPP-IV inhibition depends upon several factors, including the host, the nature and the severity of the condition being treated, the mode of administration and the particular compound employed. However, in general, conditions mediated by DPP-IV inhibition are effectively treated when a compound of formula I, or a corresponding pharmaceutically acceptable acid addition salt, is administered enterally, e.g., orally, or parenterally, e.g., intravenously, preferably orally, at a daily dosage of 0.002–5, preferably 0.02–2.5 mg/kg body weight or, for most larger primates, a daily dosage of 0.1–250, preferably 1–100 mg. A typical oral dosage unit is 0.01–0.75 mg/kg, one to three times a day.

Usually, a small dose is administered initially and the dosage is gradually increased until the optimal dosage for the host under treatment is determined. The upper limit of dosage is that imposed by side effects and can be determined by trial for the host being treated.

The compounds of formula I, and their corresponding pharmaceutically acceptable acid addition salts, may be combined with one or more pharmaceutically acceptable carriers and, optionally, one or more other conventional pharmaceutical adjuvants and administered enterally, e.g., orally, in the form of tablets, capsules, caplets, etc. or parenterally, e.g., intravenously, in the form of sterile injectable solutions or suspensions. The enteral and parenteral compositions may be prepared by conventional means.

The compounds of formula I, and their corresponding pharmaceutically acceptable acid addition salts, may be formulated into enteral and parenteral pharmaceutical compositions containing an amount of the active substance that is effective for treating conditions mediated by DPP-IV inhibition, such compositions in unit dosage form and such compositions comprising a pharmaceutically acceptable carrier.

The compounds of formula I (including those of each of the subscopes thereof and each of the examples) may be administered in enantiomerically pure form (e.g., ee≧98%, preferably ≧99%) or together with the S enantiomer, e.g., in racemic form. The above dosage ranges are based on the compounds of formula I (excluding the amount of the S enantiomer).

The following examples show representative compounds encompassed by this invention and their synthesis. However, it should be clearly understood that they are for purposes of illustration only.

EXAMPLE 1

3-[(cyclohexyl)amino]acetyl-4-cyano-(R)-thiazolidine monohydrochloride

A) Preparation of N-t-boc protected 3-[(cyclohexyl) amino]acetyl-4-amide-(R)-thiazolidine To a solution of 1.62 g (6.31 mmol) of N-t-boc protected N-cyclohexyl glycine in 18.9 ml of anhydrous tetrahydrofuiran is added, successively, 1.0 g (7.58 ml) of (R)-(-)-4-amide thiazolidine, 1.28 g (9.46 mmol) of 1-hydroxybenzotriazole hydrate and 1.97 ml of 1,3-diisopropylcarbodiimide. The resultant clear light yellow reaction mixture is then stirred at room temperature under a calcium sulfate drying tube for 21 hours. The resultant cloudy yellow solution is then concentrated via rotovap and the yellow oily sludge that forms is then partitioned between methylene chloride and water. The aqueous layer is then washed twice with 50 ml portions of methylene chloride and the combined methylene chloride layers are washed with saturated sodium chloride, dried over sodium sulfate, filtered and concentrated to yield the crude form of the desired compound as a hazy yellow oil. Purification via column chromatography employing a mixture of hexane and ethyl acetate in a 1:1 ratio as the eluant yields the desired compound as a clear oil.

B) Preparation of N-t-boc protected 3-[(cyclohexyl) amino]acetyl-4-cyano-(R)-thiazolidine In a nitrogen flushed, three-necked 100 ml flask is dissolved 1.60 g (4.31 mmol) of the compound prepared in A) above in 17.3 ml of pyridine. 0.352 g (5.17 mmol) of imidazole is then added and the clear, colorless solution is then cooled to ~−35° C. employing a dry ice/acetonitrile cooling bath. 1.04 ml (11.2 mmol) of phosphoryl chloride is then added, dropwise over a period of 6 minutes, and the resultant cloudy white reaction mixture is then stirred for 1 hour at ~−35° C. The resultant light yellow opaque mixture is then concentrated via rotovap-high vacuum pumping to remove the pyridine and obtain the crude form of the desired compound as a slightly yellow oily paste. Purification via column chromatography employing a mixture of hexane and ethyl acetate in a 1:1 ratio as the eluant yields the desired compound as a thick, light yellow taffy which crystallizes upon sitting at room temperature.

C) Preparation of the title compound in free base form

In 9.28 ml of acetonitrile is dissolved 0.665 g (1.86 mmol) of the compound prepared in B) above. 9.28 ml of trifluoroacetic acid is then added and the resultant slightly exothermic, clear, colorless mixture is stirred for 3 hours under a calcium sulfate drying tube. To the resultant clear, nearly colorless solution is added 2 ml of toluene and the mixture is concentrated via rotovap. The resultant yellow oil is then subjected to the toluene addition and subsequent concentration two more times, and vacuum pumped overnight to yield the trifluoroacetic acid salt as a clear yellow taffy. The salt is then neutralized by partitioning between methylene chloride and saturated aqueous sodium bicarbonate. The methylene chloride layer is then concentrated via rotovap to yield the desired compound as a clear light oil.

D) Preparation of the title compound

After dissolving the free base compound prepared in C) above in 50 ml of dry tetrahydrofuran, the solution is cooled in an ice-water bath and hydrogen chloride gas is bubbled into the solution for 10 seconds. The solution is then concentrated via rotovaping and vacuum pumping to obtain the title compound as a light, fluffy, yellow solid.

Preparation of the (R)-(−)-4-amide thiazolidine starting material a) Preparation of N-t-boc protected (R)-(−)-thiazolidine-4-carboxylic acid To an ice-water cooled solution of 10.0 g (75.0 mmol) of (R)-(−)thiazolidine-4-carboxylic acid, 3.3 g of sodium hydroxide (83.0 mmol), 50 ml of water and 100 ml of dioxane is added 18.0 g of di-t-butyl dicarbonate (0.083 mmol) in one portion. The initially clear solution is stirred at room temperature for 90 minutes and the resultant opaque white mixture is acidified with 2N hydrochloric acid and extracted 3 times with ethyl acetate. The combined organic extracts are then dried over sodium sulfate and concentrated via rotovap and high vacuum pumping to obtain the desired compound as a white solid.

b) Preparation of N-t-boc protected (R)-(−)-thiazolidine-4-succinic anhydride

To a solution containing the compound prepared in a) above and 100 ml of tetrahydrofuran is added 11.0 g (95.3 mmol) of N-hydroxysuccinimide followed by 12.0 g (95.2 mmol) of 1,3-diisopropylcarbodiimide. The reaction is then stirred for 2 hours at room temperature under a calcium sulfate drying tube and then partitioned between 100 ml of water and 50 ml of ethyl acetate. The aqueous layer is then washed twice with 50 ml of ethyl acetate and the combined ethyl acetate layers are dried over sodium sulfate, filtered and concentrated. Vacuum pumping yields a mixture of the desired compound and 1,3-diisopropylurea as a white solid.

c) Preparation of N-t-boc protected (R)-(−)-thiazolidine-4-amide

To an ice-water cooled solution of the mixture prepared in b) above in 150 ml of methylene chloride is bubbled in anhydrous ammonia over a period of 15 minutes. The resulting opaque white solution is then stirred for 3 hours and then partitioned between methylene chloride and water. The aqueous layer is then washed twice with 100 ml of methylene chloride. The combined methylene chloride layers are then dried over sodium sulfate, filtered and then concentrated via rotovap and vacuum pumping to yield a mixture of the desired compound and 1,3-diisopropylurea as a white taffy.

d) Preparation of the trifluoroacetic acid salt of (R)-(−)-4-amide thiazolidine

The mixture prepared in c) above is dissolved in 74.4 ml of trifluoroacetic acid and the resultant clear, yellow solution is stirred at room temperature for 2 hours under a calcium sulfate drying tube. The solution is then concentrated and the trifluoroacetic acid is chased by the addition of 20 ml of toluene and rotovaping to remove the solvent. The chasing procedure is repeated again and the resultant clear yellow oil is triturated with cold anhydrous ether and vacuum pumped to yield a mixture of the desired compound and 1,3-diisopropyl urea.

e) Preparation (R)-(−)-4amide thiazolidine

To a solution of the mixture prepared in d) above and 235 ml of tetrahydrofiran is added 42.9 g of Amberlite IRA 400 (OH) ion-exchange resin which was pre-washed with water and then tetrahydrofuran. The resultant heterogeneous reaction mixture is then stirred at room temperature for 20 minutes and filtered. The filtrate is then dried over powdered sodium sulfate, filtered, and concentrated via rotovap to yield the desired compound as a white granular solid which is essentially free of the 1,3-diisopropylurea impurity.

Preparation of the N-t-boc protected N-cyclohexyl glycine starting material a) Preparation of benzyl 2-cyclohexylamine acetate To an ice-water cooled solution of 65.8 ml of methylene chloride and 18.2 g of potassium carbonate is added 11.3 ml (98.7 mmol) of cyclohexylamine. To this mixture is added dropwise, over a period of 1 hour, a mixture of 5.21 ml (32.9 mmol) of benzyl 2-bromo-acetate and 65.8 ml of methylene chloride. The resultant hazy, white reaction mixture is then stirred at ice-water temperature for 2.5 hours and then at room temperature for 2.5 days. The resultant opaque, white reaction mixture is then partitioned between methylene chloride and water, and the methylene chloride layer is extracted. The aqueous layer is then washed twice with 50 ml portions of methylene chloride and the combined methylene chloride layers are washed with saturated aqueous sodium chloride and dried over sodium sulfate. The solution is then filtered and concentrated to yield a clear yellow liquid which is purified via column chromatography employing a mixture of hexane and ethyl acetate (1:1 ratio) as the eluant to obtain the desired compound as a clear, very light yellow liquid.

b) Preparation of N-t-boc protected benzyl-2-cyclohexylamine acetate

To an ice-water cooled solution of 58 ml of methylene chloride and the compound prepared in a) above is added, dropwise over a period of 40 minutes, a solution of 6.66 ml (28.9 mmol) of di-t-butyl dicarbonate in 58 ml of methylene chloride. The resultant clear, light yellow reaction mixture is the stirred at ice-water temperature for 1.5 hours and at room temperature for 16 hours. The reaction mixture is then partitioned between methylene chloride and aqueous sodium bicarbonate. The aqueous layer is then washed twice with 50 ml portions of methylene chloride and the combined methylene chloride extracts were washed with saturated sodium chloride, dried over sodium sulfate, filtered and concentrated to yield the desired compound as a clear, light yellow liquid.

c) Preparation of N-t-boc protected -N-cyclohexyl glycine

The compound prepared in b) above is dissolved in 105 ml of ethyl acetate and to the dissolved mixture is added 1.0 g of 10% palladium on carbon. The resultant opaque, black mixture is then shaken for 3 hours, under 45 p.s.i. of hydrogen, filtered through celite and concentrated via rotovap to yield the desired compound as a white wax.

EXAMPLE 2
3-[(3-isopropoxypropyl)amino]acetyl-4-cyano-(R)-thiazolidine monohydrochloride A) Preparation of N-t-boc protected 3-[(3-isopropoxypropyl)amino]acetyl-4-amide-(R)-thiazolidine Following essentially the procedure of Example 1A), and using in place of the N-t-boc protected N-cyclohexyl glycine, an equivalent amount of N-t-boc protected N-3-isopropoxypropyl glycine, the desired compound is obtained as a gluey solid.

B) Preparation of N-t-boc protected 3-[(3-isopropoxypropyl)amino]acetyl-4-cyano-(R)-thiazolidine Following essentially the procedure of Example 1B), and using in place of compound 1A), an equivalent amount of the compound prepared in A) above, the desired compound is obtained as a light yellow oil.

C) Preparation of the title compound in free base form

Following essentially the procedure of Example 1C), and using in place of compound 1B), an equivalent amount of the compound prepared in B) above, the desired compound is obtained as an oily paste.

D) Preparation of the title compound

Following essentially the procedure of Example 1D), and using in place of compound 1C), an equivalent amount of the compound prepared in C) above, the desired compound is obtained as a white, fluffy solid which turns to a light-orange, sticky oil upon sitting at room temperature.

EXAMPLE 3
3-[(isopropyl)amino]acetyl-4-cyano-(R)-thiazolidine monohydrochloride A) Preparation of N-t-boc protected 3-[(isopropyl)amino]acetyl-4-amide-(R)- thiazolidine Following essentially the procedure of Example 1A), and using in place of the N-t-boc protected N-cyclohexyl glycine, an equivalent amount of N-t-boc protected N-isopropyl glycine, the desired compound is obtained as a white, fluffy solid.

B) Preparation of N-t-boc protected 3-[(isopropyl)amino] acetyl-4-cyano-(R)-thiazolidine Following essentially the procedure of Example 1B), and using in place of compound 1A), an equivalent amount of the compound prepared in A) above, the desired compound is obtained as a thick, light-yellow oil.

C) Preparation of the title compound in free base form

Following essentially the procedure of Example 1C), and using in place of compound 1B), an equivalent amount of the compound prepared in B) above, the desired compound is obtained as an oil.

D) Preparation of the title compound

Following essentially the procedure of Example 1D), and using in place of compound 1C), an equivalent amount of the compound prepared in C) above, the desired compound is obtained as a light-green solid which turns light yellow upon sitting at room temperture, m.p. 202°–204° C. (dec.)

Below are the $^{13}$C NMR signals for the nitrile functionalities of the specific synthesized compounds described above:

| Compound # | $^{13}$C NMR (MHz, solvent) δ ppm (CN) |
|---|---|
| Ex. 1 | 118.25 |
| Ex. 2 | 120.32 |
| Ex. 3 | 120.54 |

What is claimed is:

1. A compound of formula I:

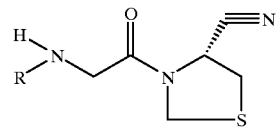

wherein
R is $C_{1-12}$alkyl; a group

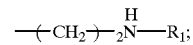

an unsubstituted $(C_{3-7})$-cycloalkyl ring; a group —(—CH$_2$—)$_2$—R$_2$; a group

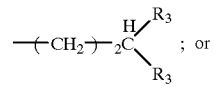

a group —(—CH$_2$—)$_3$R$_4$;

R$_1$ is an unsubstituted pyridine ring; a pyridine ring mono- or di-substituted by halo, trifluoromethyl, cyano or nitro; an unsubstituted pyrimidine ring; or a pyrimidine ring monosubstituted by halo, trifluoromethyl, cyano or nitro;

R$_2$ is an unsubstituted phenyl ring; or a phenyl ring mono-, di- or tri-substituted by halo or $(C_{1-3})$alkoxy;

each R$_3$, independently, is an unsubstituted phenyl ring; or a phenyl ring monosubstituted by halo or $(C_{1-3})$alkoxy; and R$_4$ is a 2-oxopyrrolidine group or a $(C_{2-4})$alkoxy group;

or a pharmaceutically acceptable acid addition salt thereof.

2. A compound according to claim 1 of formula 1a:

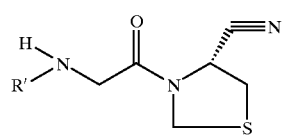

where
R' is $C_{1-10}$alkyl; a group

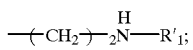

an unsubstituted $(C_{3-7})$cycloalkyl ring; or a group —(—CH$_2$—)$_3$R$_4$';

R'$_1$ is an unsubstituted pyridine ring; or a pyridine ring mono- or di-substituted by halo, trifluoromethyl, cyano or nitro; and $R_4'$ is a ($C_{2-4}$)alkoxy group;
or a pharmaceutically acceptable acid addition salt thereof.

3. A compound according to claim 2 of formula Ib:

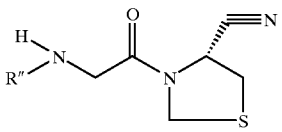

where
R″ is $C_{1-8}$alkyl; a group

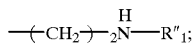

an unsubstituted ($C_{4-6}$)-cycoalkyl ring; or a group
—(—$CH_2$—)—$_3R_4'$;
$R_1″$ is a pyridine ring mono- or di-substituted by halo, trifluoromethyl
cyano or nitro; and
$R_4'$ is as defined in claim 2;
or a pharmaceutically acceptable acid addition salt thereof.

4. A compound according to claim 3 of formula Ic:

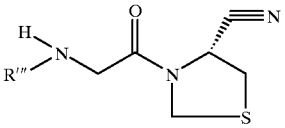

where
R‴ is $C_{1-6}$alkyl; a group

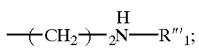

an unsubstituted ($C_{4-6}$)-cycloalkyl ring; or a group
—(—$CH_2$—)—$_3R_4'$;
$R_1‴$ is a pyridine ring monosubstitued by halo, trifluoromethyl, cyano or nitro; and
$R_4'$ is as defined above;
or a pharmaceutically acceptable acid addition salt thereof.

5. A compound according to claim 4 which is 3[(cyclohexyl)amino]acetyl-4-cyano-(R)-thiazolidine, or a pharmaceutically acceptable acid addition salt thereof.

6. A compound according to claim 5 which is 3[(cyclohexyl)amino]acetyl-4-cyano-(R)-thiazolidine monohydrochloride.

7. A compound according to claim 4 which is 3-[(3-isopropoxypropyl)amino]acetyl-4-cyano-(R)-thiazolidine, or a pharmaceutically acceptable acid addition salt thereof.

8. A compound according to claim 7 which is 3-[(3-isopropoxypropyl)amino]acetyl-4-cyano-(R)-thiazolidine monohydrochloride.

9. A compound according to claim 4 which is 3-[(isopropyl)amino]acetyl-4-cyano-(R)-thiazolidine, or a pharmaceutically acceptable acid addition salt thereof.

10. A compound according to claim 9 which is 3-[(isopropyl)amino]acetyl-4-cyano-(R)-thiazolidine monohydrochloride.

11. A pharmaceutical composition comprising a pharmaceutically acceptable carrier or diluent and a therapeutically effective amount of a compound according to claim 1, or a pharmaceutically acceptable acid addition salt thereof.

12. A pharmaceutical composition comprising a pharmaceutically acceptable carrier or diluent and a therapeutically effective amount of a compound according to claim 2, or a pharmaceutically acceptable acid addition salt thereof.

13. A pharmaceutical composition comprising a pharmaceutically acceptable carrier or diluent and a therapeutically effective amount of a compound according to claim 3, or a pharmaceutically acceptable acid addition salt thereof.

14. A pharmaceutical composition comprising a pharmaceutically acceptable carrier or diluent and a therapeutically effective amount of a compound according to claim 4, or a pharmaceutically acceptable acid addition salt thereof.

15. A pharmaceutical composition according to claim 14 comprising a therapeutically effective amount of 3-[(cyclohexyl)amino]acetyl-4-cyano-(R)-thiazolidine, or a pharmaceutically acceptable acid addition salt thereof.

16. A pharmaceutical composition according to claim 14 comprising a therapeutically effective amount of 3-[(3-isopropoxypropyl)amino]acetyl-4-cyano-(R)-thiazolidine, or a pharmaceutically acceptable acid addition salt thereof.

17. A pharmaceutical composition according to claim 14 comprising a therapeutically effective amount of 3-[(isopropyl)amino]acetyl-4-cyano-(R)-thiazolidine, or a pharmaceutically acceptable acid addition salt thereof.

18. A method of inhibiting dipeptidyl peptidase-IV comprising administering to a mammal in need of such treatment a therapeutically effective amount of a compound according to claim 1, or a pharmaceutically acceptable acid addition salt thereof.

19. A method of inhibiting dipeptidyl peptidase-IV comprising administering to a mammal in need of such treatment a therapeutically effective amount of a compound according to claim 2, or a pharmaceutically acceptable acid addition salt thereof.

20. A method of inhibiting dipeptidyl peptidase-IV comprising administering to a mammal in need of such treatment a therapeutically effective amount of a compound according to claim 3, or a pharmaceutically acceptable acid addition salt thereof.

21. A method of inhibiting dipeptidyl peptidase-IV comprising administering to a mammal in need of such treatment a therapeutically effective amount of a compound according to claim 4, or a pharmaceutically acceptable acid addition salt thereof.

22. A method according to claim 21 comprising administering a therapeutically effective amount of 3-[(cyclohexyl)amino]acetyl-4-cyano-(R)-thiazolidine, or a pharmaceutically acceptable acid addition salt thereof.

23. A method according to claim 21 comprising administering a therapeutically effective amount of 3-[(3-isopropoxypropyl)amino]acetyl-4-cyano-(R)-thiazolidine, or a pharmaceutically acceptable acid addition salt thereof.

24. A method according to claim 21 comprising administering a therapeutically effective amount of 3-[(isopropyl)amino]acetyl-4-cyano-(R)-thiazolidine, or a pharmaceutically acceptable acid addition salt thereof.

25. A method of treating conditions mediated by dipeptidyl peptidase-IV inhibition comprising administering to a mammal in need of such treatment a therapeutically effective amount of a compound according to claim 1, or a pharmaceutically acceptable acid addition salt thereof.

26. A method of treating conditions mediated by dipeptidyl peptidase-IV inhibition comprising administering to a mammal in need of such treatment a therapeutically effective amount of a compound according to claim 2, or a pharmaceutically acceptable acid addition salt thereof.

27. A method of treating conditions mediated by dipeptidyl peptidase-IV inhibition comprising administering to a mammal in need of such treatment a therapeutically effective amount of a compound according to claim 3, or a pharmaceutically acceptable acid addition salt thereof.

28. A method of treating conditions mediated by dipeptidyl peptidase-IV inhibition comprising administering to a mammal in need of such treatment a therapeutically effective amount of a compound according to claim 4, or a pharmaceutically acceptable acid addition salt thereof.

29. A method according to claim 28 comprising administering a therapeutically effective amount of 3-[(cyclohexyl)amino]acetyl-4-cyano-(R)-thiazolidine, or a pharmaceutically acceptable acid addition salt thereof.

30. A method according to claim 28 comprising administering a therapeutically effective amount of 3-[(3-isopropoxypropyl)amino]acetyl-4-cyano-(R)-thiazolidine, or a pharmaceutically acceptable acid addition salt thereof.

31. A method according to claim 28 comprising administering a therapeutically effective amount of 3-[(isopropyl)amino]acetyl-4-cyano-(R)-thiazolidine, or a pharmaceutically acceptable acid addition salt thereof.

32. A method according to claim 25 wherein the condition treated is non-insulin-dependent diabetes mellitus.

33. A method according to claim 26 wherein the condition treated is non-insulin-dependent diabetes mellitus.

34. A method according to claim 27 wherein the condition treated is non-insulin-dependent diabetes mellitus.

35. A method according to claim 28 wherein the condition treated is non-insulin-dependent diabetes mellitus.

36. A method according to claim 35 comprising administering a therapeutically effective amount of 3-[(cyclohexyl)amino]acetyl-4-cyano-(R)-thiazolidine, or a pharmaceutically acceptable acid addition salt thereof.

37. A method according to claim 35 comprising administering a therapeutically effective amount of 3-[(3-isopropoxypropyl)amino]acetyl-4-cyano-(R)-thiazolidine, or a pharmaceutically acceptable acid addition salt thereof.

38. A method according to claim 35 comprising administering a therapeutically effective amount of 3-[(isopropyl)amino]acetyl-4-cyano-(R)-thiazolidine, or a pharmaceutically acceptable acid addition salt thereof.

* * * * *